United States Patent [19]

Ensley, Jr.

[11] Patent Number: 4,520,103

[45] Date of Patent: May 28, 1985

[54] MICROBIAL PRODUCTION OF INDIGO

[75] Inventor: Burt D. Ensley, Jr., Thousand Oaks, Calif.

[73] Assignee: Amgen, Thousand Oaks, Calif.

[21] Appl. No.: 437,035

[22] Filed: Oct. 27, 1982

[51] Int. Cl.³ .................... C12N 15/00; C12N 1/20; C12N 1/00; C12P 17/10

[52] U.S. Cl. ........................... 435/121; 435/172.3; 435/317; 435/253; 435/849; 435/877; 935/29; 935/56; 935/60; 935/72; 935/73; 935/14

[58] Field of Search ............. 435/121, 172.3, 253, 435/317, 849, 877

[56] References Cited

U.S. PATENT DOCUMENTS 4,237,224  12/1980  Cohen et al. ..................... 435/317

FOREIGN PATENT DOCUMENTS 1554192  10/1979  United Kingdom .

OTHER PUBLICATIONS

Stecher et al., "The Merck Index", Merck & Co. Inc., Rahway, NJ, p. 564.
Sebek et al., "Divergent Pathways of Indole Metabolism in Chromobacterium violaceum", Nature 196, (1962), pp. 793–795.
Oshima et al., "Oxidation of Indole to Indigotin by *Pseudomonas indolixidans*", Journal of Biochemistry 58(3), (1965), pp. 259–263.
Deeley et al., "Nucleotide Sequence of the Structural Gene for Tryptophanase of *Escherichia coli* K–12", Journal of Bacteriology 147(3), (1981), pp. 787–796.
Taylor et al., "Synthesis of Tryptophanase in *Escherichia coli*: Isolation and Characterization of a Structural Gene Mutant", Molecular and General Genetics 165(1), (1978), pp. 95–102, Chem. abst. 89:193726.
Skryabin et al., "Oxidation of Naphthalene by a Strain of *Pseudomonas putida* carrying a Mutant Plasmid", Mikrobiologiya 47(2), (1978), pp. 273–277, Chemical Abstracts 89:19965c.
"Amgen's DNA Designers Fashion Blue–Jeans Gene", Biotechnology Newswatch, McGraw–Hill, NY, Dec. 5, 1983, p. 2.
Wada, "Enzymic Oxidation of Indole", Tanabe Amino Acid Res. Found. Symp. 1, (1964), pp. 93–97, Chem. Abst. 63:5960h.
Fujioka et al., "The Bacterial Oxidation of Indole", Biochemica et Biophysica Acta 159, (1968), pp. 70–78.
Grund et al., "Cloning of Genes for Naphthalene Metabolism in *Pseudomonas putida*", Journal of Bacteriology 156(1), (1983), pp. 89–94.
Ensley et al., "Oxidation of Naphthalene by a Multicomponent Enzyme System from Pseudomonas sp. Strain NCIB 9816", Journal of Bacteriology 149(3), (1982), pp. 948–954.
Schell, "Cloning and Expression in *Escherichia coli* of the Naphthalene Degradation Genes from Plasmid NAH7", Journal of Bacteriology 153(2), (1983), pp. 822–829.
Jacoby et al., "Transposition of Pseudomonas Toluene–Degrading Genes and Expression in *Escherichia coli*", Nature 274, (1978), pp. 179–180.
Ensley et al., "Expression of Naphthalene Oxidation Genes in *Escherichia coli* Results in the Biosynthesis of Indigo", Science 222, (1983), pp. 167–169.
Yen et al., "Plasmid Gene Organization: Naphthalene/-Salicylate Oxidation", Proceedings of the National Academy of Sciences 79, (2–1982), pp. 874–878.
Shimatake et al., "Purified λ Regulatory Protein cII Positively Activates Promotors for Lysogenic Development", Nature 292(1981), pp. 128–132.
Deeley et al., "Transcription Initiation at the Tryptophanase Promotor of *Escherichia coli* K–12", Journal of Bacteriology 151(2), pp. 942–951.
Botsford, J. L. et al., *J. Bacteriol.* 105: 303–312, (1971).
Gibson et al., *Biochem.*, 9: 1626–1630, (1970).
Gray, P. H., "Formation of Indigotin from Indole by Soil Bacteria," *Roy. Soc. Proc., B*, 102: 263–280, (1927).
Miles, P. et al., "The Identification of Indigo as a Pigment Produced by a Mutant Culture of *Schizophyllum commune*," *Archives of Biochemistry and Biophysics*, 62: 1–5, (1956).
Post et al., *P.N.A.S. USA*, 76: 1697–1701, (1979).
Sussman, R. et al., *Acad. Sci. Paris*, 254: 1517–1519, (1962).
Yeh et al., *Biochem. & Biophys. Res. Comm.*, 78: 401–410, (1977).
Davies et al., *Biochem. Journal*, 91: 251, (1964).
Hansen et al., *J. Bacteriol.*, 135: 227–238, (1978).
Shamsuzzamon et al., *Biochem. Biophys. Res. Comm.*, 60: 582–589, (1974).

*Primary Examiner*—Thomas G. Wiseman
*Assistant Examiner*—John Edward Tarcza
*Attorney, Agent, or Firm*—Marshall, O'Toole Gerstein, Murray & Bicknell

[57] ABSTRACT

Microbial synthesis of indigo dyestuff in indole-free media is disclosed. Indigo production is preferably accomplished by genetic transformation of selected host cells having the capacity to produce and accumulate indole (either as a result of endogenous genomic capacity or genetic transformation) to incorporate the capacity for synthesis of an aromatic dioxygenase enzyme. Growth of transformed cells under suitable conditions facilitates aromatic dioxygenase enzyme catalyzed oxidative transformation of cellular indole, with consequent formation of indigo from the oxidized reaction products. In a highly preferred embodiment, *E. coli* cells having endogenous indole production capacity are transformed with a DNA expression vector comprising the structural gene for naphthalene dioxygenase, resulting in the microbial synthesis of isolatable quantities of indigo.

14 Claims, No Drawings

MICROBIAL PRODUCTION OF INDIGO

BACKGROUND

The present invention relates generally to the microbial production of dyestuffs and more particularly to microbial production of indigo by organisms in indole-free media.

Indigo, or indigotin, occurs as a glucoside in many plants of Asia, the East Indies, Africa, and South America, and has been used throughout history as a blue dye. Principally obtained from plants of the genera Indigofera and Isatus, indigo was used to dye blue the earliest known textiles, linen mummy wrappings dating from 2000 BC. By the middle of the 19th century, indigo had become a principal item in trade between Europe and the Orient. Prior to elucidation of the structure and the synthesis of the indigo molecule, the use of natural indigo involved protracted fermentation processes to liberate the dye for introduction into fabric in a soluble, colorless form, indican. By steeping the fabric and indican in a vat, the soluble indican was easily hydrolyzed to glucose and indoxyl. Mild oxidation, such as exposure to air, would convert the indoxyl to indigo, regenerating the pigment in the fibers of the fabric.

During the 19th century considerable effort was directed towards determining the structure of this valuable compound. The chemical structure of indigo, corresponding to the formula $C_{16}H_{10}N_2O_2$, was announced in 1883 by Adolf von Baeyer after eighteen years of study of the dye. However, a commercially feasible manufacturing process was not developed until approximately 1887. The method, still in use throughout the world, consists of a synthesis of indoxyl by fusion of sodium phenylglycinate in a mixture of caustic soda and sodamide. All industrially successful processes also involve the final step of air oxidation of indoxyl to indigo. To date, indigo has been principally used for dying cotton or wool shades of navy blue. The compound also has potential use in processes for solar energy collection. [See British Pat. No. 1,554,192].

Pertinent to the background of the invention are prior observations of microbial production of a blue pigment. Using selective methods of cultivation, one experimenter in 1927 isolated a soil organism (*Pseudomonas indoloxidans*) that could decompose indole with the formation of blue crystals. The blue particles that appeared in cultures containing that bacterium were insoluble in water, alcohol, ether, xylol, and benzol, but did dissolve in strong sulfuric acid to give a blue solution which dyed silk blue. The experimenter concluded that indoxyl was probably not formed within the cells of this organism, but rather that the blue crystal formation was due to the production of an exoenzyme diffusing out from the bacterial growth. This organism could not use indole as a source of energy and could not oxidize indole to indigotin without an additional source of carbon, but could oxidize indole if given a supply of carbon. A high carbon to nitrogen ratio appeared to be most suitable to the growth of *Pseudomonas indoloxidans* and the production of indigotin. Further observations made by the experimenter were that indole appeared to depress the growth of the organism and that the organisms multiplied rapidly as soon as the indole had been consumed. The oxidation of indole was observed to take place only during the early stages of growth of the organism. No trace of indoxyl was found in cultures, and the indigotin was not apparently further oxidized to isatin. The experimenter also noted that two other soil organisms, *Mycobacterium globerulum* and *Micrococcus piltonensis*, could also produce small amounts of indigotin on indole agar only. [See: Grey, P. H., "Formation of Indigotin from Indole by Soil Bacteria," *Roy.Soc.Proc., B*, 102: 263–280 (1927)].

A single mutant culture of *Schizophyllum commune* fungus producing a "blue pigment" has also been described. The culture was grown on a chemically defined, synthetic medium containing glucose, $(NH_4)_2HPO_4$, thiamine, $KH_2PO_4$, $K_2HPO_4$, and $MgSO_4.7H_2O$. The ammonium ion was the nitrogen source. Both a red and a blue pigment were harvested from mycelial macerates. The identification of the blue pigment extracted from the macerates with chloroform was obtained by solubility tests, absorption spectroscopy, and chemical analyses. The results of these tests were all consistent with the conclusion that the blue pigment was indigo. [See: Miles, P., et al., "The Identification of Indigo as a Pigment Produced by a Mutant Culture of *Schizophyllum commune*," *Archives of Biochemistry and Biophysics*, 62: 1–5 (1956)].

In 1962, a study was performed on the biogenesis of the pigment violacein by the organism *Chromobacterium violaceum*, which readily converted L. tryptophan to violacein, but did not utilize this amino acid for growth. The experimenters created a novel microbiological assay, specific for L. tryptophan, in which the quantity of violacein produced was a function of the amount of L. tryptophan present in the test sample. It was observed that when L. tryptophan was incubated with lyophilized cells, indole was transiently formed and, after a forty-eight-hour incubation, a deep blue pigment was synthesized. The pigmented material was identified as indigo on the basis of its color, absorption spectra, and RF values in thin layer chromatography. The experimenters concluded that indoxyl was an intermediate of the indigo pathway in this bacterium, and found that *Chromobacterium violaceum* metabolized L. tryptophan to indole by the action of tryptophanase or tryptophan synthetase. This microorganism synthesized violacein not only from L. tryptophan but also from indole. When the enzymes of the violacein pathway were inactivated by rapid lyophilization, both L. tryptophan and indole were metabolized to indigo. [See: Sebek, O. and Jaeger, H., "Divergent Pathways of Indol Metabolism in Chromobacterium Violaceum," *Nature*, 196: 793–795 (1962)].

In a more recent report, experimenters isolated an organism from soil by the enrichment culture techniques using indole as the sole source of carbon and nitrogen. An aerobic gram positive coccus, which rapidly decomposed indole when grown in a medium containing indole, $KH_2PO_4$, $K_2HPO_4$, NaCl, $MgSO_4$, water, and yeast extract, produced a blue pigment which was not released into the culture medium. It was noted that the indole in the medium was used up very rapidly and more indole was added several times during the culture period. The cells, when harvested, were very blue and decomposed indole with the consumption of eleven to thirteen atoms of oxygen per mole of the substrate. When anthranilic acid, glucose or glycerol was substituted for indole in culturing the organism, the cells showed no ability to decompose indole, indicating that the activity was inducible. When grown on indole, the microorganism decomposed indole to hydroxyindole, anthranilic acid, and catachol. A cell-free extract of this organism contained an enzyme, dihydroxyindole oxygenase, which catalyzed the conversion of dihydroxyindole to anthranilate plus $CO_2$. The dihydroxyindole oxygenase was determined to be an inducible enzyme which appeared only when the organism was grown on indole. The pathway proposed for degradation of indole by these experimenters was: indole to indoxyl to dihydroxyindole to anthranilic acid to catachol. [Fujioka, M. and Wada, H., "The Bacterial Oxidation of Indole," *Biochemica et Biophysica Acta*, 158: 70–78 (1968)].

To date, none of the above organisms has been put to use in the large-scale microbial synthesis of indigo. This is likely to be due, in large part, to unfavorable economic factors involved in providing indole as a substrate or otherwise maintaining precise nutrient balances in the growth medium.

Enteric bacteria (e.g., *E.coli*) indigenous to the intestinal tracts of animals are capable of accumulating indole [see, e.g., Post, et al., *P.N.A.S. USA*, 76: 1697–1701 (1979)] by the activity of the enzyme tryptophanase produced by the tryptophanase structural gene. Tryptophanase, believed to be a catabolic enzyme, catalyzes the degradation of tryptophan, resulting in the stoichiometric production of indole, pyruvate, and ammonia. An associated enzyme, tryptophan synthetase, can also catalyze the synthesis of tryptophan, from indole glycerol phosphate, and serine. In *E.coli*, synthesis of tryptophanase is inducible by tryptophan. The tryptophanase structural gene tnaA of *E.coli* K12 has been cloned and sequenced. See, Deeley, M., et al., "Nucleotide Sequence of the Structural Gene for Tryptophanase of *E.coli* K12," *J.Bacteriology*, 147: 787–796 (1981); and Deeley, M., et al., "Transcription Initiation at the Tryptophanase Promoter of *E.coli* K12," *J.Bacteriology*, 151: 942–951 (1982). While enteric bacteria are capable of growing on simple media, they do not possess the enzymatic wherewithal to convert indole to indigo.

Of particular interest to the background of the present invention is the inventor's copending U.S. patent application Ser. No. 419,953, filed Sept. 20, 1982, entitled "Method and Materials for the Microbiological Oxidation of Aromatic Hydrocarbons," the disclosures of which are specifically incorporated by reference herein. In this copending application, the applicant describes, inter alia, a transmissible plasmid pE317 containing a DNA sequence of *Pseudomonas putida* origin which codes for expression in a host microorganism of enzymes participative in the oxidative degradation of naphthalene to salicylate. Most briefly put, the copending application discloses use of plasmids such as pE317 and others to transform microorganisms such as *E.coli* and imbue them with the capacity to produce and accumulate selected valuable intermediates ordinarily only transitorily formed in the microbial mineralization of aromatic compounds such as naphthalene. Included in the enzymes coded for by plasmid pE317 is a naphthalene dioxygenase enzyme. This enzyme catalyzes the transformation of naphthalene to cis-1,2-naphthalene dihydrodiol. Applicant and his coworkers had previously performed an exhaustive study of the oxidation of naphthalene by a multi-component enzyme system from Pseudomonas sp.NC1B 9816 [see Ensley, et al., *J.Bacteriology*, 149: 948–954 (1982)] and characterized the initial reaction in naphthalene oxidation as involving an enzyme system comprised of three protein components.

At present, therefore, the art has not been provided with any reliable description of efficient microbiological production of indigo. This is the case, despite knowledge of the existence of certain microorganisms having the capacity to synthesize and accumulate indole and certain other organisms having the capacity to employ indole as a substrate for indigo synthesis.

BRIEF SUMMARY

The present invention provides the first instance of microbiological production of indigo in a genetically-transformed microorganism grown in an indole-free medium.

In one of its aspects, the invention provides a process for microbiological production of indigo in a selected microorganism having the metabolic capacity to produce and accumulate indole. The process involves stably genetically transforming the microorganism to incorporate the capacity to synthesize one or more aromatic dioxygenase enzymes. Dioxygenase enzymes operable in the present invention are those which will catalyze microbial oxidative tranformation of an aromatic hydrocarbon to a cis-dihydrodiol. The transformed microorganisms are grown under conditions which facilitate the dioxygenase enzyme catalysis of the oxidative transformation of indole. The presumptive oxidative transformation reaction product is cis-indole-2,3-dihydrodiol. This product, in turn, is believed to rearrange to indoxyl, which then condenses to indigo in the presence of air. Indigo is then isolated from the microorganism or its growth medium.

In one of its presently most preferred forms, microbiological production of indigo in a microorganism already having the metabolic capacity to produce and accumulate indole is accomplished using *E.coli* as the host cell microorganism. Included in the genetic transformation step is transformation with a DNA vector including a DNA sequence coding for the expression of naphthalene dioxygenase, an aromatic dioxygenase enzyme of Pseudomonas origin, derived from the *P.putida* naphthalene mineralization plasmid nah7. A suitable expression vector for this purpose is pE317 described in copending application Ser. No. 419,953.

Practice of processes of the invention may include the additional steps of stably genetically transforming the microorganism to incorporate the capacity to synthesize tryptophanase enzyme and growing the microorganisms under conditions facilitative of tryptophanase catalyzed degradation of tryptophan into pyruvate and indole. Genetic transformation of host microorganisms to develop (or enhance) the capacity to synthesize tryptophanase enzyme as well as aromatic dioxygenase enzymes may be accomplished by transformation with a single DNA vector including DNA sequences coding for both types of enzymes.

The present invention thus provides processes for microbiological production of indigo in selected microorganisms which do not have the metabolic capacity to produce and accumulate indole, as well as in those that do. "Multiply-transformed" microorganisms can be grown under conditions facilitative of both tryptophanase enzyme catalysis of the transformation of tryptophan to indole, and dioxygenase enzyme catalyzed oxidative transformation of indole to an oxidized form further "processed" within the cell to indigo. Indigo can thereafter be isolated from the microorganisms and/or the surrounding culture medium.

Also provided by the present invention, therefore, are novel DNA transformation vectors comprising DNA sequences coding for microbial synthesis of both an aromatic dioxygenase enzyme and a tryptophanase enzyme. An "indigo operon" may be incorporated into a single vector, in which operon both the tryptophanase and dioxygenase enzyme coding regions are under the control of a single promoter/regulator. The promoter/regulator of the operon can enable simultaneous operation of both enzymes in the microbial host, thus creating a microbial "sink" in which continuous catalysis of tryptophan to indole, and indole to cis-indole-2,3-dihydrodiol and ultimately to indigo occurs. Desirably, the promoter/regulator would be sensitive to an inducer or a change in culture temperature.

According to still another aspect of the invention, organisms having the capacity to synthesize one or more dioxygenase enzymes (whether by means of expression of genomic or plasmid-borne DNA sequences) are genetically altered to have the capacity to produce indigo upon growth in an indole-free medium. Such genetic alteration involves stable transformation to incorporate the capacity to synthesize a tryptophanase enzyme.

Further aspects and advantages of the present invention will become apparent upon consideration of the following detailed description of presently preferred embodiments thereof.

DETAILED DESCRIPTION

The methods and materials which provide an illustration of the invention and which comprise the presently preferred embodiment relate specifically to plasmid-borne DNA sequences of *Pseudomonas putida* origin which can be employed to transform a desired indole-producing host microbial species, such as *E.coli*. Cells transformed according to this embodiment of the process and the DNA transformation vector express the DNA sequences in the form of synthesis of an initial dioxygenase enzyme (or enzyme system) which is capable of converting accumulated indole to cis-indole-2,3-dihydrodiol. The dihydrodiol, in turn, rearranges to form indoxyl, which also accumulates in the selected host microorganism. The latter product, in the presence of air, is transformed to indigo.

DNA sequences coding for dioxygenase enzymes useful in practice of the invention may be secured by recombinant methods practiced on microbial species displaying the capacity to synthesize and accumulate one or more enzymes catalyzing microbial oxidative transformation of an aromatic hydrocarbon to a cis-dihydrodiol form. Especially likely to provide DNA sequences for use in the invention are those organisms empirically determined to display the capacity to transform indole supplied to the growth medium into indigo. One such organism is *Pseudomonas putida* PpG7 containing a transmissible naphthalene degrading plasmid, nah7. This organism served as the parent strain for development of plasmid pE317 employed in the selective procedures for aromatic hydrocarbon oxidation set out in copending application Ser. No. 419,953. Also expected to provide suitable DNA sequences is *P.putida* NCIB 9816, containing a transmissible naphthalene-degrading plasmid similar to (and possibly identical to) nah7. Both these organisms have now been observed to produce indigo when indole is supplied as a component of their growth medium.

Also expected to provide useful sources of DNA sequences coding for dioxygenase enzymes for practice of the invention are those organisms possessing a capacity for oxidative mineralization of aromatic hydrocarbons other than naphthalene (e.g., toluene, benzene and the like), whether or not the gene coding for the enzyme is plasmid-borne or genomic. As examples of such organisms may be cited *Pseudomonas putida* "TOL" described by Yeh, et al., *Biochem. & Biophys. Res. Comm.*, 78: 401–410 (1977) and *P.putida* 39/D described by Gibson, et al., *Biochem.*, 9: 1626–1630 (1970). Each of these organisms displays the capacity to synthesize a dioxygenase enzyme catalyzing the formation of cis-toluene-2,3-dihydrodiol as a product of the oxidation of toluene. Each of these organisms has now been observed to display the capacity to produce indigo when indole is supplied as a component of their growth medium.

When a DNA sequence coding for a dioxygenase enzyme is transformed by an appropriate vector into a microorganism, such as *E.coli*, which has its own tryptophanase enzyme, the microorganism can produce indigo from tryptophan. The following illustrative examples treat: (1) the construction of plasmid pE317 and its predecessor pNUT; (2) the identification of the blue pigment produced by the vector-harboring microorganism of the present invention during growth in defined medium containing ampicillin; (3) the determination that naphthalene dioxygenase enzyme produced by the DNA coding region of the DNA vector is reacting with indole produced endogenously by *E.coli*; and (4) measurement of the rate of indigo synthesis by the recombinant *E. coli*.

EXAMPLE 1

Plasmid pNUT, which codes for the expression of *Pseudomonas putida* hydrocarbon degradative enzymes in an *Escherichia coli* host, was constructed by the following procedure. The plasmid Nah 7 [Yen, et al., *P.N.A.S. U.S.A.*, 79: 874–878 (1982)] was isolated from *Pseudomonas putida* pPG 7 by an alkaline-SDS procedure of Hansen, et al., *J.Bacteriol.*, 135: 227–238 (1978) and digested to completion with Hind III. The digested Nah 7 DNA was mixed with Hind III-digested pBR322 (A.T.C.C. 37017) and incubated with DNA ligase. The ligated DNA was transformed into *E.coli* HB101 and the transformed cells were plated onto L-agar containing 200 $\mu$g/ml ampicillin. The plates were incubated for 24 hours and the resultant colonies were exposed to the vapors of naphthalene crystals placed in the lid of the plate. A single colony, designated strain 625, turned brown after exposure to naphthalene vapors for 24–48 hours. Formation of the brown color indicated that strain 625 was producing one or more metabolites from naphthalene since naphthoquinone, a dark brown compound, is a by-product of naphthalene metabolism in *Pseudomonas* species [Shamsuzzamon, et al., *Biochem.-Biophys.Res.Comm.*, 60: 582–589 (1974); and Davies, et al., *Biochem.Journal*, 91: 251 (1964)]. Plasmid pNUT was isolated from strain 625. This plasmid was approximately 21,000 base pairs (21 Kb) in size and produced fragments of 4.4 Kb and 16.5 Kb in size after digestion with Hind III. The 4.4 Kb Hind III fragment had the same mobility during agarose gel electrophoresis and the same pattern of restriction enzyme fragmentation as pBR322, while the large 16.5 Kb fragment was presumed to be a portion of the Nah 7 plasmid, which carried genes coding for the synthesis of naphthalene degradative enzymes.

EXAMPLE 2

*E.coli* strain 625 was analyzed for naphthalene metabolism by measuring the accumulation of non-volatile metabolites from $^{14}C$-labelled naphthalene [Ensley, et al., *J.Bacteriol.*, 149: 949–954 (1982)]. *E.coli* strain 625 was transferred from an isolated colony to 1.0 ml of L-broth containing a 200 μg/ml ampicillin and incubated in a 13×100 mm test tube with shaking at 30° C. until the cultures had reached an optical density at 600 nm ($OD_{600}$) of 1.0–2.0. The cells were pelleted in a centrifuge at 5,000×g for 10 minutes. The cell pellet was suspended in 50 mM sodium phosphate, pH 7.0 to give a cell suspension with a measured $OD_{600}$ of 0.25. A 0.5 ml portion of the cell suspension was mixed with 5.0 μl of dimethylformamide containing 50 n moles of [$^{14}C$] naphthalene (specific activity 2.5 mCi/mmol) and incubated with shaking for 30–60 minutes at 30° C. The reaction was terminated by transferring a 20 μl aliquot of the reaction mixture to the surface of a 1.5×2 cm square of pre-coated thin layer chromatography sheet. The spotted sheet was dried under a stream of air for 15 minutes, which removed unused naphthalene, and non-volatile [$^{14}C$] naphthalene metabolites on the sheet were detected by placing the sheet in 7.0 ml of liquid scintillation counting cocktail and measuring residual radioactivity in a liquid scintillation counter. Strain 625 produced measurable levels of [$^{14}C$] naphthalene metabolites with this procedure, while no naphthalene metabolism could be detected when untransformed *E.coli* HB101, or HB101 transformed with pBR322, were analyzed.

The rate of naphthalene degradation by *E.coli* strain 625 was measured with a modification of the method described above. The cell suspension containing labelled naphthalene was sampled after 10, 20, 30 and 40 minutes of incubation, and the amount of non-volatile naphthalene metabolites produced after each time interval was determined by liquid scintillation counting. A linear increase in the formation of naphthalene metabolites over time was observed in this experiment. The results are shown in Table 1, below.

EXAMPLE 3

The metabolite(s) produced from [$^{14}C$] naphthalene by *E.coli* strain 625 were identified by the following procedure. A cell suspension containing [$^{14}C$] naphthalene as described in Example 2 was incubated for 1–12 hours. The suspension was then extracted twice with 0.5 ml volumes of ethyl acetate. The organic phases were removed and combined (neutral extract), and the cell suspension was acidified by the addition of 50 μl of 1.0M HCl. The acidified suspension was extracted twice with 0.5 ml volumes of ethyl acetate, and the organic phases were removed and combined (acid extract). The neutral and acid organic extracts were reduced to dryness under vacuum and the residues dissolved in 50 μl of ethyl acetate. A 10 μl portion of each extract was analyzed by liquid scintillation counting to determine the amount of [$^{14}C$] naphthalene metabolites which could be extracted under neutral and acidic conditions. The remainder of the extracts was applied separately to the origin of a pre-coated thin layer chromatography (TLC) sheet. In addition, standards of salicylate, salicylaldehyde, α naphthol, naphthoquinone, and cis-1,2-naphthalene dihydrodiol in ethyl acetate solutions were applied in separate spots to the sheet. The chromatogram was developed in a solvent system of chloroform/methanol/acetic acid, 40:1:2 (vol/vol). The developed chromatogram was viewed under UV light and the locations of the standards were marked. The chromatogram was then exposed to Kodak AR4 X-ray film for 24 hours and the film developed to identify the location of the [$^{14}C$] naphthalene metabolites. Over 90% of the naphthalene metabolites produced by *E.coli* strain 625 were extractable in ethyl acetate only after acidification of the cell suspension, indicating the production of an acidic metabolite. Analysis of the metabolites by TLC and autoradiography revealed that strain 625 produces, from naphthalene, a single major metabolite which is acidic and has the same relative mobility during chromatography as that of authentic salicylic acid. This data indicated that *E.coli* strain 625 carries a plasmid containing that fragment of Nah 7 DNA which codes for the synthesis of enzymes involved in the oxidation of naphthalene to salicylic acid. This fragment thus comprises at least part of the gene sequence described as the Nah operon (Yen, et al., supra), i.e., sequences coding for the three protein 1,2-naphthalene dioxygenase system, cis-1,2-dihydrodiol dehydrogenase, dihydroxy naphthalene dioxygenase, hydroxychromene carboxylate isomerase, hydroxy benzalpyruvate aldolase, and salicylaldehyde dehydrogenase. Plasmid pNUT thus includes specific DNA sequences coding for degradative enzymes which are free from operative association with sequences coding for salicylate hydroxylase or similar sequences coding for the degradation of salicylate.

EXAMPLE 4

Plasmids pE3 and pE317, which are smaller than pNUT but still carry the genes associated with the Nah operon, were constructed by the following procedure. Plasmid pNUT DNA was digested with Eco RI, which produced 5 fragments visible after agarose gel electrophoresis. The digested DNA was re-ligated to produce a population of plasmid DNA's containing a variable number of the 5 Eco RI fragments. The ligated DNA was transformed into *E.coli* HB101 and brown colonies were selected and scored as described in Example 1. One clone carried a new plasmid, designated pE3, which contained only two Eco RI sites and was 17.3 Kb in size. The plasmid was isolated and again digested with Eco RI. The large Eco RI fragment (10.9 Kb) resulting from this digestion was purified by agarose gel electrophoresis and recovered from the agarose gel with NA-45 DEAE membranes (Schleicher and Schuell, Inc., Keene, NH) used according to the manufacturer's recommendations. The purified Eco RI fragment was ligated into Eco RI-cut pBR322 DNA and transformed into *E.coli* HB101. Recombinants were selected and scored as described in Example 1. Several clones carried a new plasmid which contained pBR322 (4.4 Kb) and a 10.9 Kb insert in the Eco RI site. This plasmid (15.3 Kb) was designated pE317. *E.coli* strains carrying plasmids pE3 and pE317 were analyzed for rates and products of naphthalene metabolism (Table 1, below). Both plasmids coded for the synthesis of enzymes necessary for the metabolism of naphthalene to salicylic acid, and were expressed at detectable levels in an *E.coli* host.

TABLE 1

Rates and Products of Naphthalene Metabolism By E. Coli HB101 Containing Recombinant Plasmids

| Plasmid | Vector | Size | Oxidation Product[a] | Rate[b] |
|---------|--------|------|----------------------|---------|
| pNUT | pBR322 | 21Kb | Salicylate | 5.2 |
| pE3 | pBR322 | 17.3Kb | Salicylate | 43.4 |
| pE317 | pBR322 | 15.3Kb | Salicylate | 44.0 |

[a] Product formed through the oxidation of naphthalene
[b] Rate of product formation in nmoles/hr/ml of reaction mixture as described in Example 3.

EXAMPLE 5

Plasmid pE317 was prepared as described above. When E.coli HB101 was transformed with pE317 and grown in Luria broth containing 200 μg/ml ampicillin, a blue pigment was observed to form in the culture medium and cells after overnight incubation.

The blue pigment was purified and identified by the following procedure. E.coli HB101 containing pE317 was grown for 18 hours in two one-liter flasks containing 250 ml of mineral salts medium composed of (g/L) 10 g $K_2HPO_4$, 3.5 g $Na(NH_4)HPO_4.4H_2O$, 2.0 g citric acid.$H_2O$, 0.2 g $MgSO_4.7H_2O$ supplemented with 0.25% glucose, 25 mg/L proline and leucine, 2.0 mg/L ampicillin. The flasks were shaken at 250 RPM and kept at 30° C.

After growth, the cells were separated from the spent medium by centrifugation, resulting in a dark blue cell pellet and a clear, straw-colored supernatant. The cell pellet was extracted 8 times with 25-ml volumes of boiling chloroform. The organic extracts were pooled and the volume reduced to 10 ml under a stream of argon gas. The organic extract was dried over anhydrous sodium sulfate and applied to the top of a silica gel 60 column (2.5×5 cm) previously equilibrated in chloroform. The blue pigment was washed through the column with chloroform and 4.0 ml fractions were collected. Fractions containing blue pigment were analyzed for purity by chromatography on thin layer chromatography (TLC) sheets (EM Reagents, Silica gel 60 $F_{254}$) developed in a solvent system of chloroform:acetic acid:methanol 40:2:1 (vol/vol). Those blue fractions which contained a single UV-absorbing spot after analysis by TLC were pooled and the solvent removed under vacuum. This procedure resulted in 26 mg of dark blue crystals. The crystals were dissolved in a small volume of chloroform and subjected to analysis. The blue pigment had identical chromatographic properties, visible, ultraviolet, mass and infrared spectra to that of synthetic indigo (Kodak). This data indicates that indigo is produced by the recombinant E.coli during growth under the described conditions.

EXAMPLE 6

The indication that the enzymes synthesized from the cloned naphthalene dioxygenase genes are reacting with indole produced endogenously by E.coli is consistent with the following observations.

1. After several serial passages in nonselective (i.e., ampicillin-free) medium, the recombinant organism loses the ability to produce indigo. When these cultures are analyzed for the ability to oxidize naphthalene, a parallel loss in naphthalene oxidizing activity is observed. Since untransformed E.coli is unable to produce the blue pigment, these experiments demonstrate the essential nature of the naphthalene dioxygenase genes in blue pigment formation.

2. Blue pigment formation is enhanced if the recombinant E.coli is grown in culture medium supplemented with 10 mM tryptophan or 1 mM indole.

3. No blue pigment formation is observed if the recombinant E.coli is grown in a medium supplemented with 1% glucose. High levels of glucose cause catabolite repression of tryptophanase synthesis in E.coli [Botsford, J. L. and R. D. MeMoss, J.Bacteriol. 105: 303–312 (1971)].

4. Blue pigment formation is observed if Pseudomonas putida PpG7, which carries the naphthalene dioxygenase genes on the Nah7 plasmid, is incubated with indole in the culture medium. This organism does not possess a tryptophanase enzyme system and does not produce indole during the normal course of metabolism.

EXAMPLE 7

The rate of indigo synthesis by the recombinant E.coli was measured by the following procedure. Transformed and untransformed E.coli was grown in two flasks containing the mineral salts medium described in Example 5. Ampicillin was omitted from the mineral salts medium used to grow untransformed E.coli. Growth of the organisms was monitored by measuring the absorbance at 500 nm. Indigo synthesis was monitored by removing 1.0-ml samples from each culture at various time intervals. The cultures were extracted with 2.0 ml of ethyl acetate, centrifuged to break the emulsion, and a portion of the upper (ethyl acetate) layer was transferred to a cuvette. The optical density of each organic extract at 600 nm was measured. Indigo was empirically determined to have a visible absorption maximum at 600 nm in ethyl acetate. Easily measured synthesis of indigo during growth was observed in the culture containing the transformed cells, while no indigo synthesis could be measured in the culture containing untransformed E.coli.

The foregoing examples demonstrate that endogenous tryptophanase enzyme in E.coli cells examined converts tryptophan to indole (and, likely, pyruvate and ammonia). As a consequence of the transformation of the E.coli with a DNA vector including a DNA sequence coding for microbial synthesis of naphthalene dioxygenase, as aromatic dioxygenase, is produced within the cells. The specific intermediates formed during conversion of indole to indigo in practice of the invention have not as yet been dispositively identified. It is likely, however, that the initial product of dioxygenase enzyme catalyzed transformation of indole is cis-indole-2,3-dihydrodiol. Rearrangement of the diol yields indoxyl and condensation of indoxyl in the presence of air yields indigo.

The amount of indigo formed in such procedures can be considerably increased if the organisms are additionally transformed to stably incorporate a DNA sequence coding for the tryptophanase enzyme. See, Deeley, et al., supra.

Although E.coli has its own tryptophanase enzyme coding region, that region and its regulatory mechanism are on a chromosome providing only one copy per cell. On a high copy number DNA plasmid vector, many copies of the tryptophanase enzyme coding region may be dispersed within the cell, providing higher efficiency and a higher rate of conversion of tryptophan to indole. This increased metabolism of tryptophan should activate E.coli's endogenous tryptophan synthetase enzyme regulatory mechanism to convert indole glycerol phosphate and serine to tryptophan. When the DNA vector coding regions for both tryptophanase and dioxygenase enzymes are on the same DNA vector and under the control of the same promoter, they may both be activated simultaneously. Once the *E.coli* bacteria cells harboring such vectors are grown to an optimal level, both enzyme coding regions on the plasmid may be simultaneously activated to convert the tryptophan in the cells to indole and pyruvate, and the indole to indoxyl and ultimately to indigo until all of the tryptophan produced in the cells is consumed. The indigo so produced frequently crystallizes in the medium as well as within the cells themselves, and may be extracted by simple chemical and mechanical methods.

Where the host microorganism does not have endogenous metabolic capacity to produce and accumulate indole, the transformation of the microorganisms by the DNA vector containing both DNA sequences coding for tryptophanase enzyme and an aromatic dioxygenase enzyme will function to enable the microorganism to initially convert typtophan to indole, and thereafter convert indole to indigo.

In a preferred form, an "indigo operon" DNA transformation vector of the invention would contain both tryptophanase and dioxygenase enzymes under simultaneous control of a promoter/regulator. One such indigo operon, like pE317, may consist of a small portion of the *P.putida* naphthalene mineralization plasmid nah7, which includes operon-containing DNA fragments retaining the capacity to direct naphthalene dioxygenase enzyme expression. Associated with the dioxygenase gene on the DNA transformation vector would be a tryptophanase enzyme coding region such as described by Deeley, et al., supra.

An example of a temperature sensitive promoter/regulator potentially useful in construction of such an indigo operon is phage λPL under cI 857 control. This highly efficient promoter (PL) can be regulated by the λ repressor protein cI, a product which is regulated autogenously in *E.coli* λ lysogens. Mutant repressor protein cI 857 inactivates the PL promoter at temperatures below 32° C. At temperatures between 32° C. and 41° C., cI 857 is inactivated, thereby turning on transcription under control of the PL promoter. See: Shimatake, H., et al., *Nature,* 292: 128-131 (1981); and Sussman, R., et al., *Acad. Sci.Paris,* 254: 1517-1519 (1962). While the benefits of use of a temperature sensitive promoter/regulator in coordination of cell growth and gene expression are abundantly clear, they must be considered in the light of potential drawbacks in terms of diminished activity of tryptophanase and/or dioxygenase.

The foregoing illustrative examples and detailed description have principally been directed to securing indigo production by organisms lacking the genetic wherewithal to "process" indole in a manner leading to the formation of indigo, i.e., lacking the capacity to synthesize a suitable dioxygenase enzyme. It will be apparent to those skilled in the art that the present invention also comprehends securing production of indigo by cultured growth of organisms already having the capacity to synthesize a suitable dioxygenase enzyme. This is accomplished by genetic transformation of such organisms to stably incorporate DNA sequence(s) specifying synthesis of a tryptophanase enzyme, thus allowing for processing and transformation of cellular tryptophan into an indole substrate for action of the dioxygenase enzyme. As was the case with augmenting the endogenous tryptophanase synthesizing capacity of an organism by inserting multiple "extra" copies of a tryptophanase gene, substantial benefits are expected to attend augmenting the endogenous dioxygenase synthesizing capacity of selected host cells by insertion of multiple copies of a plasmid comprising an "indigo operon."

At present, the best prospective host cells for practice of this aspect of the invention are the *Pseudomonas putida* previously discussed as appropriate sources of dioxygenase gene, i.e., PpG7, NCIB 9816, "TOL" and 39/D.

Numerous other modifications and variations of the invention as above-described are expected to occur to those skilled in the art and consequently only such limitations as appear in the appended claims should be placed thereon.

What is claimed is:

1. A process for microbial production of indigo in a selected microorganism having the metabolic capacity to produce and accumulate indole, said process comprising:
    (1) stably genetically transforming the microorganism with an exogenous DNA sequence to incorporate the capacity to synthesize an aromatic dioxygenase enzyme capable of participating in the formation of indigo from indole;
    (2) growing transformed microorganisms under conditions facilitative of dioxygenase enzyme catalyzed oxidative transformation of indole; and
    (3) isolating indigo produced by said microorganisms.

2. The process of claim 1 wherein the microorganism is *E.coli.*

3. The process of claim 1 wherein said genetic transformation step includes transformation with a DNA vector including a DNA sequence coding for synthesis of an aromatic dioxygenase enzyme.

4. The process of claim 1 wherein the aromatic dioxygenase enzyme is naphthalene dioxygenase.

5. The process of claim 1 wherein the aromatic dioxygenase enzyme is of Pseudomonas origin.

6. The process of claim 1 further including the step of stably genetically transforming the microorganism to incorporate the capacity to synthesize tryptophanase enzyme and growing the transformed microorganism under conditions facilitative of tryptophanase enzyme catalysis of the degradation of tryptophan into indole, pyruvate and ammonia.

7. The process of claim 6 wherein both recited transformations are accomplished by transformation with a single DNA vector including DNA sequences coding for synthesis of aromatic dioxygenase enzyme and tryptophanase enzyme.

8. The process of claim 7 wherein expression of both enzyme coding sequences is under the control of a single selected promoter/regulator DNA sequence.

9. The process of claim 8 wherein the promoter/regulator DNA sequence is a phage λPL temperature sensitive sequence.

10. A DNA transformation vector comprising DNA sequences coding for microbial synthesis of an aromatic dioxygenase and tryptophanase enzymes.

11. A DNA transformation vector according to claim 10 wherein said DNA sequences are under the control of the same promoter/regulator DNA sequence.

12. A process for microbial production of indigo in a selected microorganism which does not have the metabolic capacity to produce and accumulate indole, said process comprising:

(1) stably genetically transforming with an exogenous DNA sequence the microorganism to incorporate the capacity to synthesize tryptophanase enzyme;

(2) stably genetically transforming the microorganism to incorporate the capacity to synthesize an aromatic dioxygenase enzyme capable of participating in the formation of indigo from indole;

(3) growing transformed microorganisms under conditions facilitative of tryptophanase enzyme catalysis of the transformation of tryptophan to indole and dioxygenase enzyme catalysis of the oxidative transformation of indole; and (4) isolating indigo produced by said microorganisms.

13. The process of claim 12 wherein said genetic transformation steps includes transformation with a single DNA vector including DNA sequences coding for synthesis of tryptophanase and aromatic dioxygenase enzymes.

14. The process of claim 13 wherein said DNA sequences are under control of the same promoter/regulator DNA sequence.

* * * * *